US008642082B2

(12) United States Patent
Ajani et al.

(10) Patent No.: US 8,642,082 B2
(45) Date of Patent: Feb. 4, 2014

(54) PHARMACEUTICAL COMPOSITIONS FOR THE ORAL ADMINISTRATION OF HEPARIN OR DERIVATIVES THEREOF

(75) Inventors: Mauro Ajani, Lainate (IT); Luigi Moro, Lainate (IT); Roberto Villa, Lainate (IT)

(73) Assignee: Cosmo Technologies Limited, Wicklow (IE)

( * ) Notice: Subject to any disclaimer, the term of this patent is extended or adjusted under 35 U.S.C. 154(b) by 1585 days.

(21) Appl. No.: 10/498,095

(22) PCT Filed: Dec. 3, 2002

(86) PCT No.: PCT/EP02/13651
§ 371 (c)(1),
(2), (4) Date: Jun. 10, 2004

(87) PCT Pub. No.: WO03/049721
PCT Pub. Date: Jun. 19, 2003

(65) Prior Publication Data
US 2005/0020539 A1    Jan. 27, 2005

(30) Foreign Application Priority Data
Dec. 11, 2001 (IT) .............................. MI2001A2599

(51) Int. Cl.
*A61K 9/22* (2006.01)
*A61K 9/26* (2006.01)
*A61K 9/14* (2006.01)
*A61K 31/727* (2006.01)

(52) U.S. Cl.
USPC .............. 424/468; 424/469; 424/486; 514/56

(58) Field of Classification Search
USPC ............................... 424/468, 469, 486; 514/56
See application file for complete search history.

(56) References Cited

U.S. PATENT DOCUMENTS

| 5,665,370 A * | 9/1997 | Gehret et al. ................. 424/413 |
| 5,665,379 A | 9/1997 | Herslöf et al. |
| 6,380,173 B1 * | 4/2002 | Stutzmann et al. ............. 514/56 |
| 2003/0036568 A1 * | 2/2003 | Raoof et al. .................. 514/772 |

FOREIGN PATENT DOCUMENTS

| JP | 60-054313 | 3/1985 |
| JP | 02-223533 | 5/1990 |
| JP | 06-024961 | 1/1994 |
| JP | 07-002648 | 6/1995 |
| WO | WO 99/39700 | 8/1999 |
| WO | WO 99/56731 | * 11/1999 | ............... A61K 9/22 |
| WO | WO 00/48589 A | 8/2000 |
| WO | WO 00/76481 | * 12/2000 |
| WO | WO 00/76481 A1 | 12/2000 |

OTHER PUBLICATIONS

Celasco, G., et al; "Clinical trial: oral colon-release pamaparin sodium tablets (CB-01-05 MMX®) for active left-sided ulcerative colitis"; *Aliment Pharmacol. Ther.*; vol. 31; pp. 375-386 (2010).

Pastorelli, L., et al; "Oral, colonic-release low-molecular-weight heparin: an initial open study of Parnaparin-MMX for the treatment of mild-to-moderate left-sided ulcerative colitis"; *Aliment Pharmacol. Ther.*, vol. 28; pp. 581-588 (2008).
Swenson, E.S., et al; "Means to enhance penetration—Intestinal permeability enhancement for proteins, peptides and other polar drugs: mechanisms and potential toxicity"; *Advanced Drug Delivery Reviews*; vol. 8; pp. 39-92 (2 pgs); Reference 3 (1992).
Korzenik, J.R.; "Clinical Trials and Therapeutics, IBD: A Vascular Disorder? The Case for Heparin Therapy"; *Inflammatory Bowl Diseases®*; vol. 3, No. 2, pp. 87-94 (1997).
Brazier, F., et al; "Treatment of Ulcerative Colitis with Heparin"; *Gastroenterology*, vol. 110, No. 4, A872, AGA Abstracts, 1996.
Dupas, J.L., et al; "Treatment of Active Crohn's Disease with Heparin"; *Gastroenterology*, vol. 110, No. 4, A900, AGA Abstracts, 1996.
Folwaczny, C., et al; Heparin in the Treatment of Highly Active Inflammatory Bowel Disease (IBD); *Gastroenterology*, vol. 110, No. 4, A908, AGA Abstracts (1996).
Evans, R.C., et al; "Treatment of Corticosteroid Resistant Ulcerative Colitis with Heparin—A report of 9 cases"; *Gut 37 (suppl. 2)*, vol. 37, F194, Clinical Practice F193-F199 (1995).
Evans, R.C., et al; "Treatment of corticosteroid-resistant ulcerative colitis with heparin—a report of 16 cases"; *Aliment Pharmacol Ther*, vol. 11, pp. 1037-1040 (1997).
Gaffney, P.R., et al; "Paradoxical Response to Heparin in 10 Patients with Ulcerative Colitis"; *The American Journal of Gastroenterology*, vol. 90, No. 2, pp. 220-223 (1995).
Törkvist, L., et al; "Low molecular weight heparin as adjuvant therapy in active ulcerative colitis"; *Aliment Pharmacol Ther*, vol. 13, pp. 1323-1328 (1999).
Malhotra, S., et al; "A comparison of observational studies and controlled trials of heparin in ulcerative colitis"; *Int 'l Journal of Clinical Pharmacology and Therapeutics*, vol. 42, No. 12, pp. 690-694 (2004).
Shen, J., et al; "Meta-analysis: the utility and safety of heparin in the treatment of active ulcerative colitis"; *Aliment Pharmacology Therapeutics*, vol. 26, pp. 653-663 (2007).
Celasco, G., et al; T1115; "Colon-Release Parnaparin Sodium Tablets (Cb-01-05 MMX®) for Active Left-Sided Ulcerative Colitis: A Randomized, Double-Blind Controlled Study Versus Placebo"; Presented at DDW in Chicago held from May 30 to Jun. 4, 2009, 1 pg.
Rosette, C., et al; W1616; "Anti-Inflammatory and Immunomodulatory Activities of Parnaparin Sodium (CB-01-05)"; Presented at DDW in Chicago held from May 30 to Jun. 4, 2009, 1 pg.
Pastorelli, L., et al; "Safety and Efficacy of Oral, Colonic-Release, Low Molecular Weight Heparin-MMX™ for the Treatment of Mild to Moderate Left-Sided Ulcerative Colitis: Preliminary Report of a Pilot Study"; *Abstracts/Digestive and Liver Disease*, vol. 39S, pp. S139-S343 (2007).
Celasco, G., et al; "Efficacy of Intracolonic Administration of Low-Molecular-Weight Heparin CB-01-05, Compared to Other Low-Molecular-Weight Heparins and Unfractionated Heparin, in Experimentally Induced Colitis in Rat"; *Dig. Dis. Sci.*; vol. 53, pp. 3170-3175 (2008).
Baumgart, DC.; "CB-01-05-MMX, a novel oral controlled-release low molecular weight heparin for the potential treatment of ulcerative colitis", Abstract, PubMed; *Curr. Opin. Investig. Drugs*, vol. 11, No. 5, pp. 571-576 (2010).

* cited by examiner

*Primary Examiner* — Aradhana Sasan
(74) *Attorney, Agent, or Firm* — Nixon & Vanderhye

(57) ABSTRACT

Pharmaceutical compositions suitable for the oral administration of heparin or derivatives thereof, particularly controlled-release oral pharmaceutical compositions containing heparin with different molecular weight, for the treatment of inflammatory bowel diseases and related conditions, are disclosed.

11 Claims, No Drawings

PHARMACEUTICAL COMPOSITIONS FOR THE ORAL ADMINISTRATION OF HEPARIN OR DERIVATIVES THEREOF

This application is the U.S. national phase of international application PCT/EP02/13651, filed 3 Dec. 2002, which designated the U.S.

The present invention relates to pharmaceutical compositions suitable for the oral administration of heparin or derivatives thereof for the treatment of inflammatory bowel diseases.

More particularly, the invention relates to controlled-release oral pharmaceutical compositions containing heparin (either unfractioned or low molecular weight heparins) capable of selectively releasing the active ingredient in the intestine.

Chronic inflammatory bowel diseases (IBD), such as ulcerative colitis and Crohn's disease, involve therapeutical problems which have still to be satisfactorily solved. The use of the medicaments available to date, such as aminosalicylates and pro-drugs thereof, steroids, immunosuppressive agents, is often restricted by the important side effects involved as well as by the sometime insufficient effectiveness.

Safer, more effective medicaments than those presently available are therefore particularly needed.

Recently, the use of heparin has been suggested in the IBD parenteral treatment: in fact, although IBD etiology has still to be clarified, its pathogenesis is somewhat clearer, and this can account for the use of heparin in this disease.

In particular, the thrombophilic state frequently observed in ulcerative colitis favours intravasal district coagulation, which is confirmed by the presence of sub-mucosal micro-thrombosis and by vasculytic phenomena on the mesenteral vessels; furthermore, important inflammatory conditions are always present, which can be related with an alteration of both the immune system and the Th1/Th2 balance, which are mediated by interleukins (IL-1), TNF and numerous other pro-inflammatory cytokines.

All these considerations suggest the presence of vascular damage associated with, or consequent to, inflammatory conditions on an immune base, in the pathogenesis of ulcerative colitis.

Clinical studies have confirmed the therapeutical activity of heparin administered parenterally, usually through subcutaneous injection, in the treatment of IBD (Aliment. Pharmacol. Ther. 1997; 11:1037-1040; Inflammatory Bowel Diseases, 1997; 3(2): 87-94; Gastroenterology, 1996; 110:A872; Gastroenterology, 1996; 110.A 900; Gastroenterology, 1996; 110. A908, Gut, 1995; 137(S2):F194; Am. J. Gastroenterol. 1995; 90:220-223).

In these clinical studies, heparin was always administered intravenously or subcutaneously, namely through the conventional administration routes of choice for heparins and other glycosaminoglycan derivatives, which usually are not absorbed orally. Studies have been carried out for alternative administration routes to the injective one, such as the oral administration, which is by far suitable for self-medication for use in the antithrombotic therapy. However, heparin and low molecular weight derivatives thereof, when administered orally, are absorbed in insufficient amounts to attain an effective concentration and usually only in the first tract of intestine.

On the other hand, considering the chronic nature of IBD, the oral administration would be much preferable, as the treatment is usually long-term.

Formulations studied to increase heparin absorption in the gastro-intestinal tract are described in WO-A-01/34114 and WO-A-00/48589.

According to the invention, controlled-release formulations containing heparin or low molecular weight derivatives thereof have now been found, which can be administered through the oral route and are particularly suitable for the treatment of IBD, in that they provide the gradual release of heparin in the intestinal tract in correspondence with the inflamed intestinal mucosa and therefore a rapid, effective therapeutical response.

The formulations of the invention have also the advantage of preventing or slowing down any degradation and depolymerization of the molecule by the digestive juices, in the first tract of the transit of the medicament to reach the intestinal tract, where its therapeutical action has to be exerted.

The controlled-release compositions of the invention consist of a multi-matrix structure comprising:

a) a matrix consisting of amphiphilic compounds and lipophilic compounds, with melting point lower than 90° C., in which the active ingredient is at least partially englobated;

b) an outer hydrophilic matrix, in which the amphiphilic/lipophilic matrix is dispersed;

c) optionally, other excipients.

"Heparin" herein means both unfractioned heparins of various origin, and low molecular weight heparins, typically ranging from 1,000 to 10,000 Da, such as enoxaparin, fraxiparin, dalteparin, parneparin, their salts and/or derivatives and the like, and other glycosaminoglycans such as heparan sulfates, dermatan sulfates and hyaluronates. Preferably, the compositions of the invention contain optionally salified heparins (sodium or calcium heparin) or low molecular weight heparins.

The compositions of the invention, containing heparin or low molecular weight heparins or other glycosaminoglycans, can be prepared with a method comprising the following steps:

a) First, heparin is embedded in by kneading or mixing or is coated with amphiphilic compounds, which will be precised below. Mixing can be carried out without using solvents or with small amounts of water-alcoholic solvents.

b) The matrix from a) is added in a low melting lipophilic excipient or mixture of excipients, with heating to soften and/or melt the excipient in which the active ingredient is thus dispersed. The inert matrix resulting from cooling to room temperature can be reduced in size to obtain inert matrix granules containing the active ingredient particles.

c) The granules of inert+amphiphilic matrix are then mixed with one or more hydrophilic excipients which swell in the presence of water, thus increasing their volume to form a hydrated, highly viscous layer in which the solvent progress is slowed down. The mixture of powders and matrix granules is then subjected to compression or compaction so that, when the tablet is contacted with biological fluids, a swollen, highly viscous layer forms, which coordinates the solvent molecules and acts as a barrier against the penetration of the aqueous fluid inside the new structure. Said barrier antagonizes the starting "burst effect" deriving from the dissolution of the medicament present inside the inert matrix, which is in turn inside the hydrophilic matrix.

Amphiphilic compounds for use according to the invention comprise polar lipids of type I or II (lecithin, phosphatidyl-choline, phosphatidyl-ethanolamine), ceramides, glycol alkyl ethers such as diethylene glycol monomethyl ether (Transcutol®), polyoxyethylated castor oil, polysorbates, phosphoacetylcholine, sodium laurylsulfate, fatty acids sucroesters, polyethylene glycols.

The lipophilic matrix consists of compounds selected from unsaturated and/or hydrogenated fatty acids and salts, esters or amides thereof; fatty acids mono-, di- or triglycerids of polyoxyethylated derivatives thereof, waxes, cholesterol derivatives, long chain alcohols or mixtures thereof, whose melting point ranges from 40° to 90° C.

If desired, a fatty acid calcium salt dispersed in an hydrophilic matrix prepared with alginic acid can be englobated inside the lipophilic matrix, to markedly increase the hydrophilic matrix viscosity, due to penetration of the solvent until contacting the lipophilic matrix granules dispersed therein.

According to an embodiment of the invention, a pharmaceutical composition for the oral administration of heparin is obtained, by preparing first an inert, amphiphilic matrix with high content in heparin, typically ranging from 5 to 95% w/w, through dispersion of heparin in amphiphilic compounds, such as lecithin, other polar lipids of type II, surfactants or diethylene glycol monoethylene; the resulting mixture is then mixed or kneaded, usually while hot, with lipophilic compounds suitable to form an inert matrix, for example saturated or unsaturated fatty acids, such as palmitic, stearic, myristic or oleic acids, cetyl alcohol, glyceryl behenate, glyceryl palmitostearate, or mixtures thereof with other fatty acids having shorter chain, or salts or derivatives of the cited fatty acids, alone or in combination with waxes, ceramides, cholesterol derivatives or other apolar lipids in various ratios, selected so that the melting or softening points of the lipophilic compounds mixtures range from 40° to 90° C.

The resulting lipophilic/amphiphilic matrix is then reduced into granules by an extrusion and/or granulation process, or by other known processes which keep the macro-homogeneous matrix dispersion structure of the starting mix.

The hydrophilic matrix to add subsequently consists of hydrogels, i.e. substances which, when passing from the anhydrous to the hydrated state, undergo the so-called molecular relaxation, characterized by a marked increase in volume and weight following coordination of a large number of water molecules by the polar groups present in the polymeric chains of the hydrogels.

Examples of hydrogels for use according to the invention are compounds selected from acrylic or methacrylic acids polymers or copolymers, alkyl vinyl polymers, hydroxyalkyl celluloses, carboxyalkyl celuloses, polysaccharides, dextrins, pectins, starches and derivatives, natural or synthetic gums, alginic acid.

Hydrophilic compounds having bio-adhesive properties can further be used advantageously.

The granules of lipophilic/amphiphilic matrix containing the active ingredient are mixed with the above cited hydrophilic compounds in weight ratios typically ranging from 100:0.5 to 100:20 (lipophilic matrix: hydrophilic matrix). Part of the heparin can optionally be mixed with the hydrophilic compounds to obtain compositions in which the active ingredient is dispersed both in the lipophilic matrix and in the hydrophilic matrix, said compositions being preferably in the form of tablets, capsules and/or mini-matrices.

The compression of the mixture consisting of lipophilic/amphiphilic matrix, hydrogel-forming compound and optional active ingredient not embedded in the lipophilic matrix, as well as any functional excipients, produces a structure macroscopically homogeneous throughout its volume, namely a matrix containing a dispersion of the lipophilic and amphiphilic granules in a hydrophilic matrix.

Oral solid forms such as tablets, capsules, matrix granules or mini-matrices obtainable according to the invention can be optionally subjected to conventional coating processes with gastro-resistant films, such as methacrylic acids polymers (Eudragit®) or cellulose derivatives, such as cellulose acetophthalate and hydroxypropyl methylcellulose phthalate.

The compositions of the invention ensure the controlled release of the heparin or heparin derivative into the last part of small intestine and colon, wherein the antithrombotic, anti-inflammatory, immunomodulating and endothelium-regulating activities of heparin on the intestinal mucosa and submucosa provide an effective treatment of both active phases and relapses of ulcerative colitis, Chron's disease, sigmoiditis, proctitis and aspecific bowel inflammatory diseases.

For the envisaged therapeutical uses, suitable doses of heparin can range from 5 to 1000 mg per single administration, one to three times a day, with a daily dosage preferably ranging from 5 to 1000 mg.

The following examples illustrate the invention in greater detail.

EXAMPLES 1-7

Heparin Tablets for the Controlled-Release in the Colon

| Components | Um | Ex. 1 | Ex. 2 | Ex. 3 | Ex. 4 | Ex. 5 | Ex. 6 | Ex. 7 |
|---|---|---|---|---|---|---|---|---|
| Active ingredient | | | | | | | | |
| Unfractioned heparin | mg | 50 | 150 | 250 | 500 | 700 | 85 | 1000 |
| Lipophilic component | | | | | | | | |
| Cetyl alcohol | mg | 15 | | | | 20 | | |
| Stearic acid | mg | | 65 | | | | | 140 |
| Glyceryl behenate | mg | | | 100 | | | | |
| Hydrogenated castor oil | mg | | | | 54 | | | |
| Glyceryl palmitostearate | mg | | | | | | 12 | |
| White wax | mg | | | | | | | 10 |
| Carnuba wax | mg | | | | | 20 | 1 | |
| Amphiphilic component | | | | | | | | |
| Soy lecithin | mg | 10 | | | | | | |
| Phosphoacetylcholine | | | 10 | | | | | |
| Sodium laurylsulfate | | | | 25 | | | | 10 |
| Polysorbate | | | | | 10 | | 1 | 10 |
| Poe castor oil | | | | | | 15 | 1 | |

-continued

| Quali-quantitative composition for each tablet | | | | | | | | |
|---|---|---|---|---|---|---|---|---|
| Components | Um | Ex. 1 | Ex. 2 | Ex. 3 | Ex. 4 | Ex. 5 | Ex. 6 | Ex. 7 |
| Hydrophilic polymer | | | | | | | | |
| Sodium carboxymethylcellulose | mg | 50 | | | | 10 | | |
| Hydroxypropyl methylcellulose | mg | | 150 | | | | 20 | |
| Hydroxypropyl cellulose | mg | | | 200 | | | | 200 |
| Hydroxyethyl cellulose | mg | | | | 168 | | | |
| Hydroxymethyl cellulose | mg | | | | | 200 | | |
| Glidant | | | | | | | | |
| Talc | mg | 10 | 12 | 10 | 15 | 15 | 1.5 | 20 |
| Anhydrous colloidal silica | mg | 20 | 28 | 10 | 5 | 5 | 0.5 | 10 |
| Lubricant | | | | | | | | |
| Magnesium stearate | mg | 10 | 10 | 10 | | | 1 | 15 |
| Hydrogenated castor oil | mg | | | | 30 | 30 | 2 | |
| Diluent | | | | | | | | |
| Mannitol | mg | 550 | | | | | | |
| Mocrocrystalline cellulose | mg | | 225 | | 200 | | | |
| Lactose monohydrate | mg | | | 345 | | | | |
| Dibasic calcium phosphate | mg | | 200 | | 218 | | | |
| Calcium carbonate | mg | | | | | 150 | | |
| Coating | | | | | | | | |
| Acrylic polymers | mg | 32 | 32 | 32 | 32 | 32 | 3.2 | 32 |
| Talc | mg | 15 | 15 | 15 | 15 | 15 | 1.5 | 15 |
| Triethyl citrate | mg | 3.2 | 3.2 | 3.2 | | | 0.3 | 3.2 |
| Dibutyl phthalate | mg | | | | 3.2 | 3.2 | | |
| Titanium dioxide | mg | 6 | 6 | 6 | 6 | 6 | 0.6 | 6 |
| Iron oxide | mg | 3 | 3 | 3 | 3 | 3 | 0.3 | 3 |
| Polyethylene glycol 600 | mg | 1 | 1 | 1 | 1 | 1 | 0.1 | 1 |

EXAMPLES 8-14

Heparin Tablets for the Controlled-Release in the Colon

Examples 8-14

| Quali-quantitative composition per each tablet | | | | | | | | |
|---|---|---|---|---|---|---|---|---|
| Components | Um | Ex. 8 | Ex. 9 | Ex. 10 | Ex. 11 | Ex. 12 | Ex. 13 | Ex. 14 |
| Active ingredient | | | | | | | | |
| LMW heparin (MW range 2000-10000) | mg | 100 | 15 | 250 | 500 | 700 | 8.5 | 1000 |
| Lipophilic component | | | | | | | | |
| Cetyl alcohol | mg | 50 | | | | 20 | | |
| Stearic acid | mg | | 6.5 | | | | | 140 |
| Glyceryl behenate | mg | | | 100 | | | | |
| Hydrogenated castor oil | mg | | | | 54 | | | |
| Glyceryl palmitostearate | mg | | | | | | 1.2 | |
| White wax | mg | | | | | | | 10 |
| Carnauba wax | mg | | | | | 20 | 0.1 | |
| Amphiphilic component | | | | | | | | |
| Soy lecithin | mg | 10 | | | | | | |
| Phosphoacetylcholine | | | 1 | | | | | |
| Sodium laurylsulfate | | | | 25 | | | | 10 |
| Polysorbate | | | | | 10 | | 0.1 | 10 |
| Poe. castor oil | | | | | | 15 | 0.1 | |
| Hydrophilic polymer | | | | | | | | |
| Sodium carboxymethylcellulose | mg | 50 | | | | 10 | | |
| Hydroxypropyl methylcellulose | mg | | 15 | | | | 2 | |

-continued

| Components | Um | Ex. 8 | Ex. 9 | Ex. 10 | Ex. 11 | Ex. 12 | Ex. 13 | Ex. 14 |
|---|---|---|---|---|---|---|---|---|
| Quali-quantitative composition per each tablet | | | | | | | | |
| Hydroxypropyl cellulose | mg | | | 200 | | | | |
| Hydroxyethyl cellulose | mg | | | | 168 | | | |
| Hydroxymethyl cellulose | mg | | | | | 200 | | |
| *Glidant* | | | | | | | | |
| Talc | mg | 10 | 1.2 | 10 | 15 | 15 | 0.15 | 20 |
| Anydrous colloidal silica | mg | 20 | 2.8 | 10 | 5 | 5 | 0.05 | 10 |
| *Lubricant* | | | | | | | | |
| Magnesium strearate | mg | 10 | 1 | 10 | | | 0.05 | 15 |
| Hydrogenated castor oil | mg | | | | 30 | 30 | 0.2 | |
| *Diluent* | | | | | | | | |
| Mannitol | mg | 550 | | | | | | |
| Microcrystalline cellulose | mg | | 22.5 | | 200 | | | |
| Lactose monohydrate | mg | | | 345 | | | | |
| Dibasic calcium phopshate | mg | | 20 | | 218 | | | |
| Calcium carbonate | mg | | | | | 150 | | |
| *Coating* | | | | | | | | |
| Acrylic polymers | mg | 32 | 3.2 | 32 | 32 | 32 | 0.32 | 32 |
| Talc | mg | 15 | 1.5 | 15 | 15 | 15 | 0.15 | 15 |
| Trietyl citrate | mg | 3.2 | 0.3 | 3.2 | | | 0.05 | 3.2 |
| Dibutyl phthalate | mg | | | | 3.2 | 3.2 | | |
| Titanium dioxide | mg | 6 | 0.6 | 6 | 6 | 6 | 0.06 | 6 |
| Iron oxide | mg | 3 | 0.3 | 3 | 3 | 3 | 0.03 | 3 |
| Polyethylene glycol 600 | mg | 1 | 0.1 | 1 | 1 | 1 | 0.02 | 1 |

EXAMPLE 15

2 Kg of sodium Parnaparin are mixed with 100 g of stearic acid, 150 g of sodium laurylsulfate and 40 g of magnesium stearate before being compacted by compression. The resulting slugs are forced through a granulator fitted with a mesh screen suited to break the compacted granules to 2 mm maximum size; then 500 g of hydroxypropyl methylcellulose, 1000 g of microcrystalline cellulose, 1000 g of lactose, 130 g of colloidal silica and 80 g of magnesium stearate are added. After thoroughly mixing, the powders are tabletted with a biconvex tooling to unitary weight of about 500 mg. The resulting cores are then placed in a coating pan and coated with a gastro-protective film containing methacrylic copolymers of type A and B, titanium dioxide, talc, triethyl citrate, iron oxides and polyethylene glycol. The resulting tablets showed the characteristic slow dissolution profile, releasing the active ingredient linearly and progressively in about 8 hours.

EXAMPLE 16

1.2 Kg of sodium Parnaparin are mixed with 50 g of stearic acid, 100 g of sodium cholate and kneaded with a solution containing an acrylic polymer. After granulation through a 3 mm screen and subsequent drying, 200 g of high viscosity hydroxypropyl methylcellulose, 50 g of carboxyvinyl polymer, 500 g of lactose, 500 g of microcrystalline cellulose, 80 g of colloidal silica and 70 g of magnesium stearate are added. After thoroughly mixing, the powders are tabletted to unitary weight of about 250 mg using a rotary tabletting machine. The resulting cores, after gastro-resistent film-coating with acrylic copolymers of type A and B, titanium dioxide, talc, triethyl citrate, iron oxides and polyethylene glycol, showed a progressive dissolution curve in simulated enteral juice with about 30% of active ingredient released in the first 2 hours, and at least 80% in the first 8 hours.

EXAMPLE 17

600 g of sodium Parnaparin are mixed with 20 g of stearic acid, 10 g of wax, 25 g of soy lecithin and kneaded with a solution containing a medium-viscosity cellulose derivative. After granulation through a 2 mm screen and subsequent drying, 200 g of sodium carboxymethyl cellulose, 400 g of lactose, 550 g of microcrystalline cellulose, 50 g of colloidal silica and 30 g of magnesium stearate are added. After thoroughly mixing, the powders are tabletted to unitary weight of about 200 mg using a rotary tabletting machine. The resulting cores, after gastro-resistent film-coating with acrylic copolymers of type A and B, titanium dioxide, talc, triethyl citrate, iron oxides and polyethylene glycol, showed a progressive dissolution curve in simulated enteral juice with less than 40% of active ingredient released in the first 2 hours, and at least 80% in the first 8 hours.

The invention claimed is:
1. An oral pharmaceutical composition for the controlled release of heparin or a derivative thereof, consisting essentially of:
   a) a lipophilic/amphiphilic matrix consisting of amphiphilic compounds and lipophilic compounds with a melting point lower than 90° C. in which the heparin or derivative thereof is at least partially dispersed, said amphiphilic compounds being selected from polar lipids of type I or II, glycol alkyl ethers, polyoxyethylenated castor oil, polysorbates, phosphoacetylcholine, sodium laurylsulfate, fatty acids sucroesters and polyethylene glycols;

b) a hydrophilic matrix in which the lipophilic/amphiphilic matrix is dispersed;

c) other excipients suitable for solid pharmaceutical forms; and d) a gastro-resistant coating;

wherein the heparin or derivative thereof is dispersed both in the hydrophilic matrix and in the lipophilic/amphiphilic matrix;

wherein the oral composition is in the form of tablets, capsules or mini-matrices; and wherein the dosage range of heparin or derivative thereof is 5-1000 mg per single dose.

2. The composition as claimed in claim 1, wherein the lipophilic compounds are selected from unsaturated and/or hydrogenated fatty acids, the salts, esters or amides thereof, fatty acids mono-, di- or triglycerids, polyoxyethylated derivatives thereof, waxes, cholesterol derivatives, and long chain aliphatic alcohols.

3. The composition as claimed in claim 1, wherein the hydrophilic matrix consists of hydrogel-forming compounds.

4. The composition as claimed in claim 1, wherein the hydrophilic matrix consists of compounds selected from acrylic or methacrylic acids polymers or copolymers, alkyl vinyl polymers, hydroxyalkyl celluloses, carboxyalkyl celluloses, polysaccharides, dextrins, pectins, starches and derivatives, alginic acid, natural or synthetic gums.

5. The composition as claimed in claim 1, wherein the gastro-resistant coating consists of methacrylic acid polymers or cellulose derivatives.

6. The composition as claimed in claim 1, wherein the compounds which form the hydrophilic matrix have bioadhesive properties.

7. The composition as claimed in claim 1, wherein the heparin or derivative thereof is selected from heparin, sodium heparin, calcium heparin, sodium parnaparin, heparin with molecular weight ranging from 1,000 to 10,000 Da, heparan sulfates, dermatan sulfates, hyaluronates.

8. The composition according to claim 7, wherein the heparin or derivative thereof is sodium parnaparin.

9. A process for the preparation of the composition of claim 1, which comprises:

a) kneading or mixing the heparin with the lipophilic and amphiphilic compounds in the absence of solvents or in water-alcoholic solvents;

b) mixing the granules from step a) with the hydrophilic excipients and subsequent compression and compaction;

c) gastro-protective film-coating the oral solid forms from step b).

10. The composition as claimed in claim 1, wherein the polar lipids of type I or II are selected from lecithin, phosphatidylcholine and phosphatidylethanolamine, and the glycol alkyl ether is diethylene glycol monomethyl ether.

11. The composition as claimed in claim 1, wherein the dosage range of heparin or derivative thereof is 5-500 mg per single dose.

* * * * *